United States Patent [19]

Okada et al.

[11] Patent Number: 5,179,198

[45] Date of Patent: Jan. 12, 1993

[54] GLYCOPROTEIN AND GENE CODING THEREFOR

[75] Inventors: Hidechika Okada, 1-5-1 Hoshikuma, Jonan-ku, Fukuoka-shi, Fukuoka-ken; Noriko Okada, Fukuoka; Yoichi Nagami, Yokohama; Kazuhiro Takahashi, Machida; Hisao Takizawa, Machida; Jun Kondo, Machida, all of Japan

[73] Assignees: Hidechika Okada; Mitsubishi Corporation, both of Japan

[21] Appl. No.: 376,828

[22] Filed: Jul. 7, 1989

[30] Foreign Application Priority Data

Jul. 11, 1988 [JP] Japan .................. 63-172187
May 23, 1989 [JP] Japan .................. 1-129944

[51] Int. Cl.⁵ .............................. C07K 15/14
[52] U.S. Cl. ........................... 530/395; 530/827
[58] Field of Search .................. 530/350, 395

[56] References Cited

U.S. PATENT DOCUMENTS 4,132,769  1/1979  Osther .................. 424/1

OTHER PUBLICATIONS

Kozlov et al. 1989. Mol. Biol. (Moscow) 23(2): 372–378, (abstract).
Okada et al. 1989. Biochem. Biophys. Res. Commun. 162(3): 1553–1559.
Y. Sugita et al., J. Biochem. 104, 633–637 (1988).
I. Stefanova, et al., Mol. Immunol. 26, 153–161 (1989).
N. Okada et al., International Immunol. 1, 205–208 (1989).
M. H. Holguin et al., J. Clin. Invest. 84, 7–17 (1989).
H. Okada et al., Biochem. Biophys. Res. Comm. 162, 1553–1559 (1989).

*Primary Examiner*—Garnette D. Draper
*Assistant Examiner*—Keith C. Furman
*Attorney, Agent, or Firm*—David G. Conlin; David S. Resnick

[57] ABSTRACT

The present invention provides a glycoprotein derived from human cell membrane, which has a molecular weight of 20 to 25 Kd as estimated by SDS polyacrylamide gel electrophoresis, and contains N-glycoside type carbohydrate chain and phosphatidylinositol, and possesses an inhibitory activity to complement-mediated cell membrane damage. The present invention further provides a gene coding for the glycoprotein, and a method for the production of the glycoprotein and the gene therefor.

1 Claim, 8 Drawing Sheets

| Met | Gly | Ile | Gln | Gly | Gly | Ser | Val | Leu | Phe | Gly |
| Leu | Leu | Leu | Val | Leu | Ala | Val | Phe | Cys | His | Ser | Gly |
| His | Ser | Leu | Gln | Cys | Tyr | Asn | Cys | Pro | Asn | Pro | Thr |
| Ala | Asp | Cys | Lys | Thr | Ala | Val | Asn | Cys | Ser | Ser | Asp |
| Phe | Asp | Ala | Cys | Leu | Ile | Thr | Lys | Ala | Gly | Leu | Gln |
| Val | Tyr | Asn | Lys | Cys | Trp | Lys | Phe | Glu | His | Cys | Asn |
| Phe | Asn | Asp | Val | Thr | Thr | Arg | Leu | Arg | Glu | Asn | Glu |
| Leu | Thr | Tyr | Tyr | Cys | Cys | Lys | Lys | Asp | Leu | Cys | Asn |
| Phe | Asn | Glu | Gln | Leu | Glu | Asn | Gly | Gly | Thr | Ser | Leu |
| Ser | Glu | Lys | Thr | Val | Leu | Leu | Leu | Val | Thr | Pro | Phe |
| Leu | Ala | Ala | Ala | Trp | Ser | Leu | His | Pro | | | |

Fig. 1

| | | | | | | | | | | |
|---|---|---|---|---|---|---|---|---|---|---|
| Leu | Met | Gly | Ile | Gln | Gly | Gly | Val | Leu | Phe | Gly |
| His | Gly | Ile | Val | Leu | Ala | Val | Cys | His | Ser | Gly |
| Ala | Leu | Val | Gln | Cys | Tyr | Asn | Pro | Asn | Pro | Thr |
| Phe | Leu | Gln | Lys | Thr | Ala | Val | Cys | Ser | Ser | Asp |
| Val | Cys | Lys | Cys | Leu | Ile | Thr | Ala | Gly | Ser | Gln |
| Phe | Ala | Cys | Lys | Cys | Trp | Lys | Glu | His | Leu | Asn |
| Leu | Asn | Lys | Val | Thr | Thr | Arg | Arg | Glu | Leu | Glu |
| Phe | Asp | Val | Tyr | Cys | Cys | Lys | Asp | Asp | Lys | Asn |
| Ser | Tyr | Tyr | Gln | Leu | Glu | Asn | Gly | Gly | Cys | Leu |
| Ala | Glu | Gln | Thr | Val | Leu | Leu | Val | Leu | Ser | Phe |
| Leu | Lys | Thr | Ala | Trp | Ser | Leu | His | Pro | Pro | |
| | Ala | Ala | Leu | | | | | | | |

Fig. 2

```
GGG  GGT  ACT  GAT  CAA  AAT  GAG  AAC  TTA  TTT
TTC  TCA  CCA  TCT  TTA  TGC  AAT  TGT  TCC  CCA
CTG  CAT  AAC  TCA  GGG  CAT  GAA  CTG  ACA  ACT  TAA
GTC  TGC  CCT  TGT  GCT  GAG  AGG  GAC  GGG  GTG  CCC
TCT  TTC  TGT  AAT  AAA  TTT  TTG  AAG  GGT  CTG  CAT
GGG  GTC  AAC  GTC  ACC  AAG  CGC  AAG  AAT  CTG  CTT
GGA  GCT  TAC  GCC  ATT  TGG  ACC  TGC  GAA  CTT  AGC
CAA  CTG  TGC  ACA  CTC  TGT  ACA  TGC  CTT  GTT  TGG
ATC  GTC  CAG  AAA  TGT  AAG  GTC  TAC  CAG  ACA  GCC
GGA  CTC  CTG  TGC  GCG  AAC  GAC  TAC  GAA  AAA  GCA
ATG  CTG  AGC  GAC  GAT  TAT  AAC  ACG  AAC  GAG  GCA
CTG  CAT  GCT  TTT  GTG  TTC  CTA  TTT  TCA  CTG
```

Fig. 3

CAGTGTTATAATTGCCTAA

CCCAACTGCTGACTGCAAAA

CAGCCGTCAATTGTTCATCT

GATTTTGATGCGTGTCTCAT

TACCAAAGCTGGGTTACAAG

TGTATAACAAGTGTTGGAAG

TTCGAGCACTG

GLYCOPROTEIN AND GENE CODING THEREFOR

BACKGROUND OF THE INVENTION

1. Field of the Invention

The present invention relates to a novel glycoprotein possessing activity of inhibiting complement-mediated cell membrane damage, and to a gene coding for the glycoprotein.

2. Description of the Prior Art

Complement is a reaction system which includes a group of proteases being present in blood and body fluids. In response to invasion of exogeneous (non-self) substances into the body, activation of the complement system will take place and part of complement components that have been deposited on the exogeneous substances will then actively eliminate them by, for example, facilitating phagocytosis by phagocyte as well as inducing immune cytolysis. Furthermore, various peptide fragments which have been produced in the pathways of the complement activation may act upon a variety of cells. That is, they will activate lymphocytes and promote migration of neutrophils and degranulation of mast cells, thereby taking part in diverse immune and inflammatory reactions.

Although, complement may promptly react with foreign substances, its activation does not proceed on autologous normal cells. In inflammatory parts of such diseases as rheumatoid arthritis, systemic lupus erythematosus and glomerulo nephritis, however, it is generally thought that complement recognizes a self tissue as a foreign one and reacts with cell membranes of the self tissue. Consequently, complement may induce inflammatory reaction, and at the same time it may facilitate phagocytosis by phagocytes or cause cytolysis, thereby leading to cytotoxicity and aggravation of the inflammatory condition.

In recent years, it has been shown that proteins which are capable of inhibiting self-complement activation are present on cell membrane (Mol. Immunol., 20, 1233-1236 (1983)), several of which have been identified as a protein having with this function. For example, Decay Accelerating Factor (DAF) with a molecular weight of 68 Kd (J. Exp. Med., 160, 1558-1578 (1984)) and Homologous Restriction Factor (HRF) with a molecular weight of 65 Kd (PNAS, 83, 6975-6979 (1986)) have been obtained as complement inhibiting factors present on the human cell membrane. Precise function of DAF and HRF in vivo, nevertheless, has been not yet clarified in detail.

The present inventors have studied to find a membrane protein capable of inhibiting the complement activation on the self-cell membrane, besides the above factors.

Previously, the present inventors prepared a number of antibody-producing hybridomas by hybridizing spleen cells from mice immunized with human erythrocytes with mouse myeloma cells (P3U1) in the presence of polyethyleneglycol. These hybridomas were repeatedly screened to select those producing an antibody (in a supernatant of culture medium) which causes hemolysis of neuraminidase-pretreated human erythrocytes in the presence of human complement, succeeding in cloning a hybridoma producing such monoclonal antibody, which was designated as 1F5 (Proc. Gen. Conf. Jpn. Soc. Immunol., 17, 498 (1987), and Abstracts, Symposium on Complement, 24, 180 (1987)).

SUMMARY OF THE INVENTION

As a result of an extensive research on an antigen recognized by 1F5 antibody, the present inventors have found as the antigen a novel glycoprotein with a molecular weight of 20-25 Kd which is distinct from the previously reported complement-inhibiting factors.

Furthermore, in order to mass-produce said glycoprotein by recombinant DNA technique, the present inventors have successfully isolated a gene coding for the glycoprotein. The present inventions have thus been completed.

An object of the present invention, therefore, is to provide a glycoprotein derived from human cell membrane, characterized by having a molecular weight of 20-25 Kd as estimated by SDS-polyacrylamide gel electrophoresis (SDS-PAGE), by containing N-glycoside type carbohydrate and phosphatidylinositol, and by possessing activity of inhibiting cell membrane damage caused by complement.

It is another object of this invention to provide a gene coding for the above glycoprotein.

It is a further object of this invention to provide a method for the production of the glycoprotein and gene coding therefor.

BRIEF DESCRIPTION OF THE DRAWING

FIG. 1 illustrates the amino acid sequence of the 1F5 antigen protein.

FIG. 2 shows the base sequence of cDNA coding the 1F5 antigen protein, wherein " - - - " represents the complementary base sequence to the upper base sequence. The last "TAA" represents a terminal codon of the cDNA.

FIG. 3 shows the base sequence of a DNA fragment obtained by PCR method.

The solid curve (—) in the FIG. 2 represents a negative control, i.e. nonspecific adsorption of FITC-labeled mouse IgG onto MT2 cells.

Figure 6:
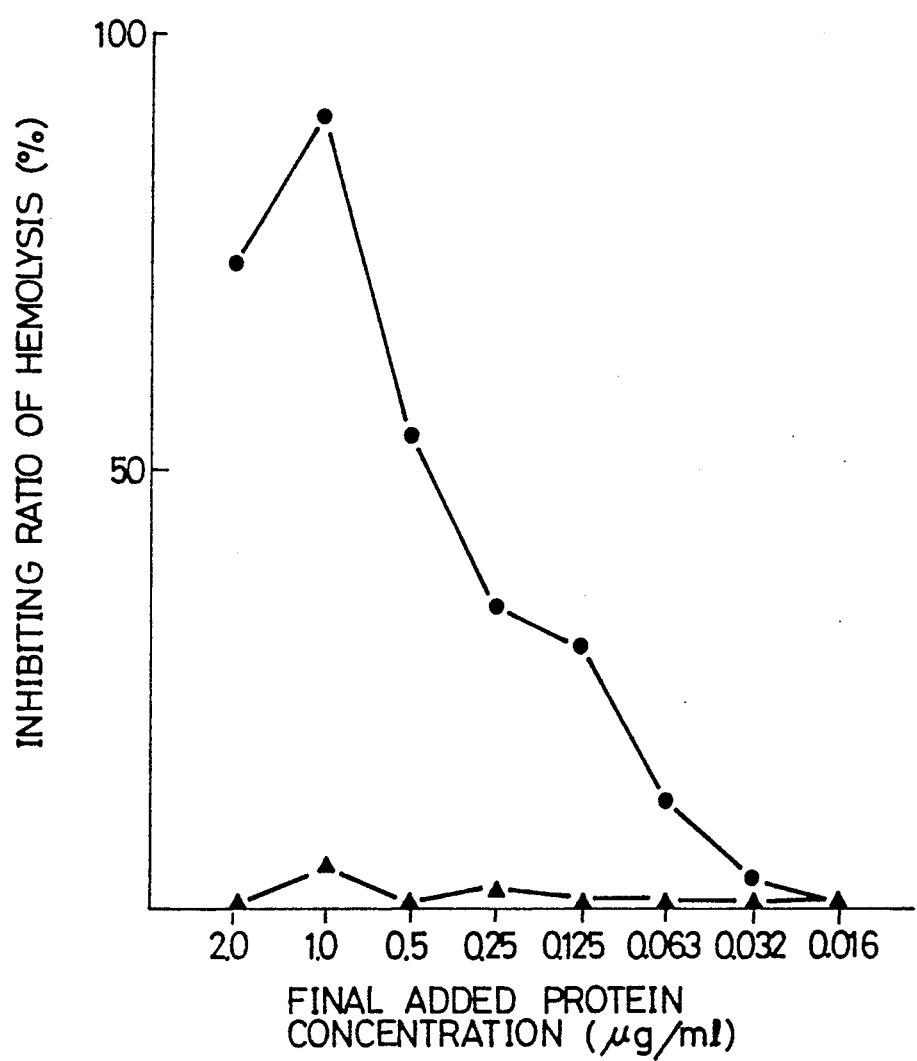

FIG. 6 shows the inhibitory activity of the glycoprotein of this invention (-.-) on human complement. mediated hemolysis of guinea pig erythrocytes, compared with that of bovine serum albumin (-Δ-).

Figure 7:
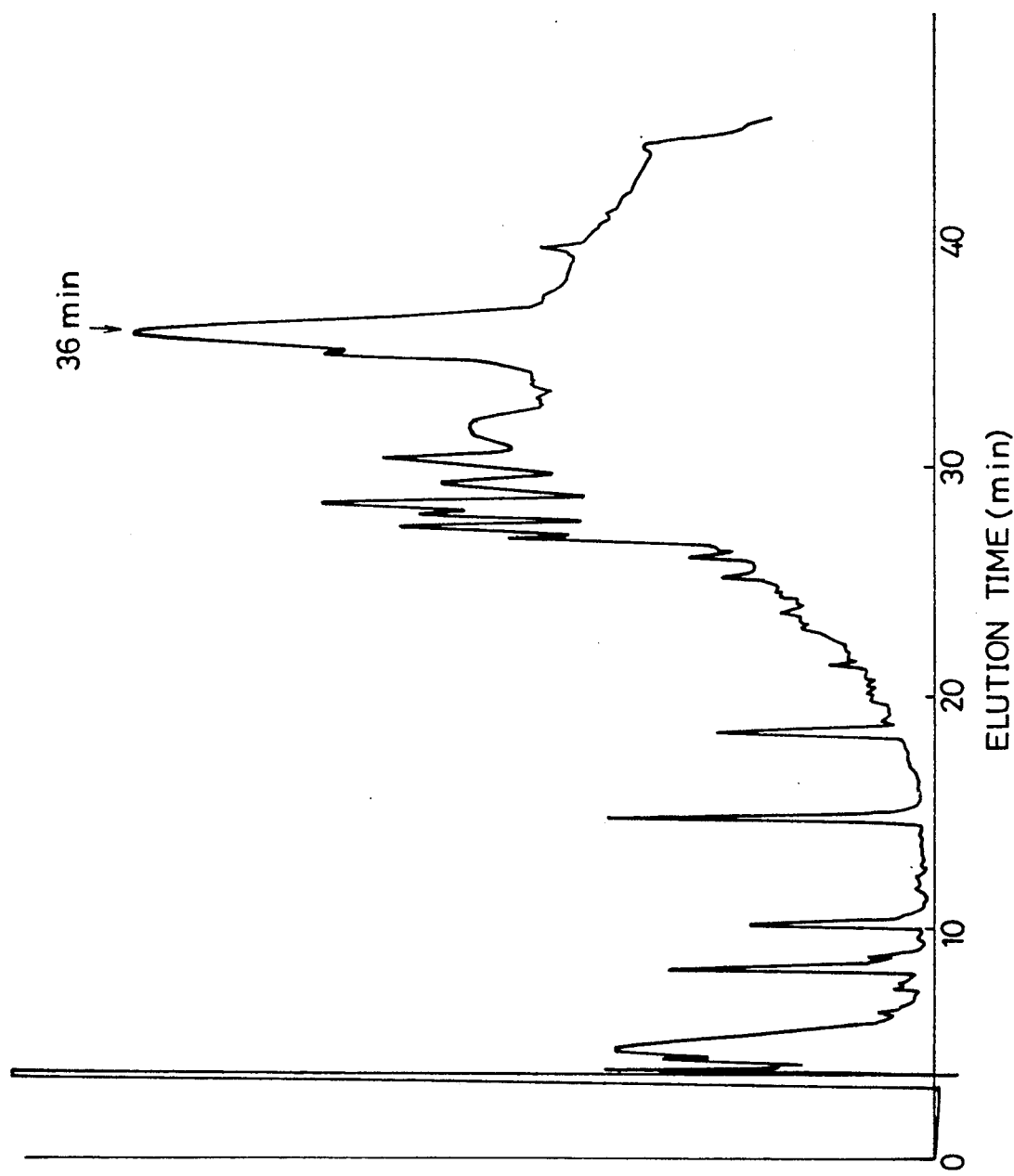
Figure 8:
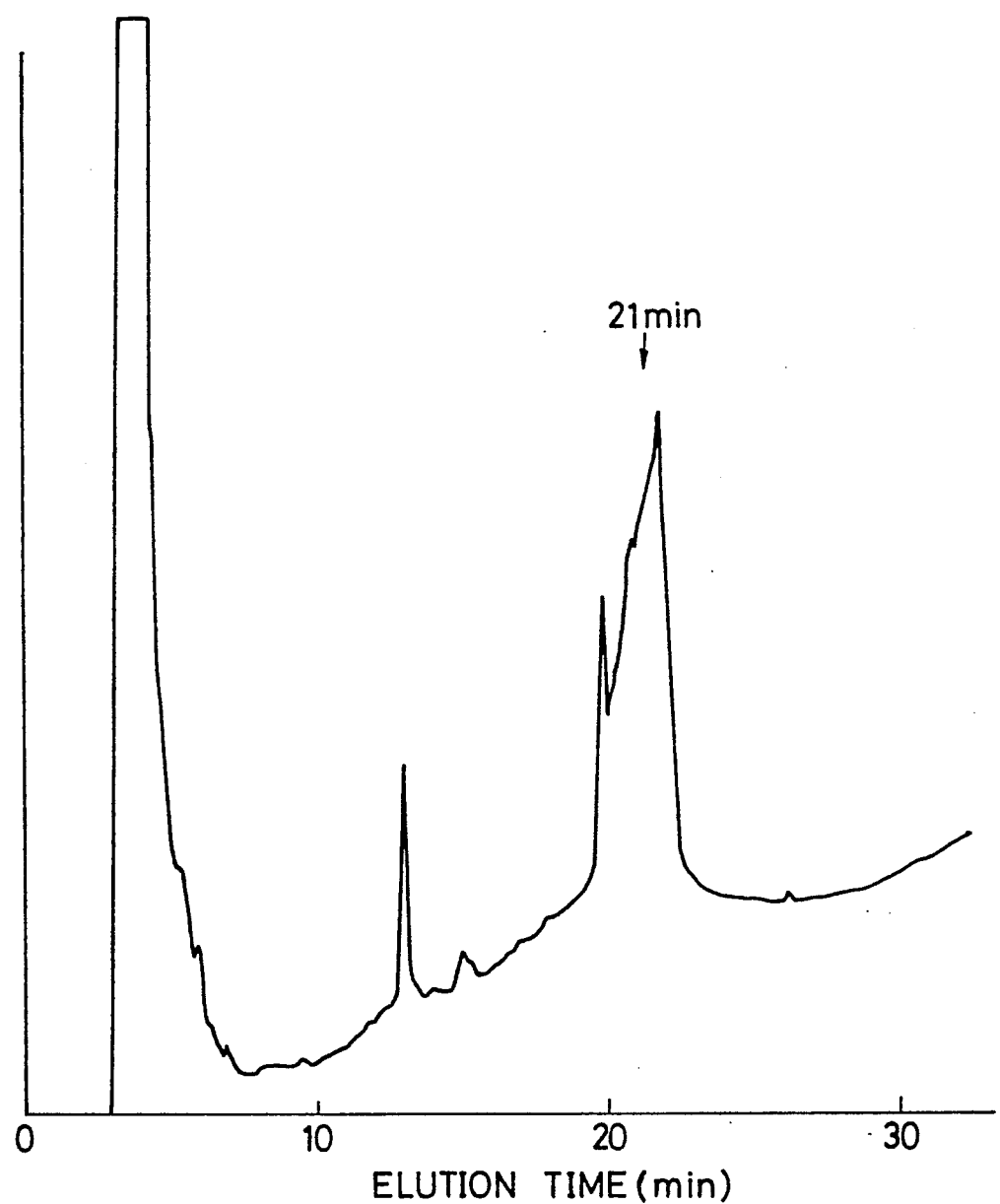

FIGS. 7 and 8 show elution patterns on reverse phase high-performance liquid chromatography, where the abscissa represents the elution time in minutes.

PREFERRED EMBODIMENTS OF THE INVENTION

The invention will hereafter be described in detail.

The glycoprotein according to the present invention may be prepared from human cell membrane as a starting material, such as that, for example, of human erythrocytes, lymphocytes, vascular endothelial cells, or tumor cells and normal human cell lines of any of these cell origins. Human cells, e.g. human erythrocytes, collected by centrifugation (at 500×g for 10 minutes approx.) are washed, for example, with Dulbecco's phosphate buffered saline (Nissui Pharmaceutical Co., Ltd.; referred to hereinafter as "PBS") and disrupted in a hypotonic solution or by other means such as disruption with nitrogen gas pressurization. To the disrupted cell suspension thus obtained, a hypotonic solution, e.g. 10 mM Tris-HCl buffer (pH 7.5) containing 1 mM -phenylmethyl-sulfonyl fluoride (PMSF) (Sigma Chemical Co.) and 1 mM EDTA, is added and the mixture is centrifuged (at 5000–10000×g for 30 minutes approx.). This procedure is repeated to obtain a cell membrane fraction.

Membrane protein may be then extracted from the washed cell membrane fraction thus prepared with the above-mentioned buffer solution further containing a detergent, e.g. β-N-octyl-glucoside (Dojin Co., Ltd.) at a concentration of about 1%, or an organic solvent, e.g. approximately 20% (v/v) butanol. Ammonium sulfate is added to the resultant membrane protein extract, and the protein fraction precipitating between 30 and 60% saturation with ammonium sulfate is collected by centrifugation.

The above fraction of precipitate with ammonium sulfate is dissolved in a small amount of the above buffer solution, and the resulting solution is subjected to an appropriate combination of column chromatographies to obtain a purified preparation of the glycoprotein of the present invention. The column chromatographies applicable for this purification process may include DEAE-Sepharose column chromatography, Mono S-column chromatography, hydroxyapatite column chromatography, phenylsepharose column chromatography and TSK2000SW (Tosoh Inc.) column chromatography. Inhibitory activity to hemolysis of guinea pig red cells by human complement may be taken as an indication of the purification degree.

Otherwise, the present glycoprotein may be obtained in the following manner. Affinity Sepharose is prepared in a usual manner using 1F5 antibody obtained by the method described in the Proceedings of the General Conference of Japan Society of Immunology 17, 498 (1987) and Abstracts of Symposium on Complement 24, 180 (1987), and the above-described ammonium sulfate-precipitated membrane protein fraction is subjected to the affinity chromatography and eluted with 0.1M glycine-HCl buffer (pH 3.0) containing 0.15M sodium chloride and 0.1% CHAPS (Sigma Chemical Co.) to purify the glycoprotein of the present invention. Meanwhile, 1F5 antibody is freely obtainable without any limitation from the Department of Microbiology, Fukuoka University School of Medicine, Fukuoka, Japan.

It may also be practicable to obtain a purified preparation of the glycoprotein of the present invention by the procedure as follows: After synthesizing a peptide with the below-described amino acid sequence corresponding to a partial amino acid sequence of the glycoprotein obtained by the method described above, rabbits are immunized with said synthesized peptide, and an IgG fruction is purified from their antisera. The above amnonium sulfate-precipitated fraction is then subjected to affinity chromatography on a column of said IgG-bound Sepharose and eluted with 0.1M glycine-HCl buffer (pH 2.8).

(a) Leu-Gln-Cys-Tyr-Asn-Cys-Pro-Asn-Pro
(b) Thr-Ala-Asp-Cys-Lys-Thr-Ala-Val

The glycoprotein of this invention thus obtained has the following properties:

(1) Its molecular weight is 20 to 25 Kd as estimated by electrophoresis (12.5% SDS-PAGE);

(2) Its carbohydrate chain contains N-glycoside type carbohydrate chains;

(3) It contains phosphatidylinositol;

(4) It has an inhibitory activity to cell damage by complement. This activity may be confirmed by the fact that, for example, the said glycoprotein is readily taken up by guinea pig erythrocytes so as to inhibit lysis (hemolysis) by complement.

(5) Isoelectric focusing with Ampholyne (Pharmacia) of pI 3.5 to 10 in the first dimension and with SDS. PAGE (12.5%) under non-reductive condition in the second dimension demonstrated formation of bands at pI values of about 5.0 (main band) and about 6.5.

(6) It has the following amino acid composition;

Asp;20.2%, Thr;8.9%, Ser;3.1%,
Glu;10.6%, Gly;2.2%, Ala;6.2%,
Cys;0.6%, Val;4.5%, Ile;1.4%,
Leu;10.1%, Tyr;8.1%, Phe;6.4%,
Lys;9.1%, His;2.1%, Arg;3.0%,
Pro;3.5%

(7) It has the following partial amino acid sequence;

Leu—Gln—Cys—Tyr—Asn—Cys
—Pro—Asn—Pro—Thr—Ala—Asp
—Cys—Lys—Thr—Ala—Val—X—X
—Ser—Ser—Asp—Phe—Asp—Ala
—X—Leu—X—Thr—Lys—Ala—Gly
—X—Gln—Val—Thr—Asn—Lys—X— where X represents Cys or other amino acid residue.

The glycoprotein of the present invention obtained as described above may be made use of, for example, for the following purposes:

(1) A stable polyclonal or monoclonal antibody to a membrane protein which has important function in the regulation of complement activity may be obtained by immunizing such animals as rabbits or mice with the glycoprotein provided by the present invention.

(2) Determination of the present glycoprotein located on the cell surface of erythrocytes, lymphocytes or other cells by the use of the antibody for the said glycoprotein makes possible the diagnosis of various diseases such as, for example, pernicious anemia, rheumatoid arthritis, systemic lupus erythematosus and glomerular nephritis.

(3) The glycoprotein of the present invention may be used as drugs for the treatment of various disorders such as inflammation in which complement activation is involved.

(4) The use of the antibody mentioned above may be applied to treatments such as those aimed at lysis of cancer cell or elimination of malignant cells.

One example of the glycoprotein provided by the present invention is a protein composed of 128 amino acids as shown in FIG. 1, which is referred to hereinafter as "1F5 antigen". In the present invention, however, those which are altered by deletion or modification of some of the constituent amino acids, or by addition of amino acids, or other insofar as such alterations cause no impairment of the function of inhibiting complement-mediated cell membrane damage, may be included as the glycoprotein of this invention.

The gene coding for the above 1F5 antigen may be exemplified by the one possessing the base sequence shown in FIG. 2. In the Figure, only one strand of the base sequence is shown with the opposite complementary base sequence being omitted and expressed only as " - - - ".

DNA fragments of the gene coding for the protein which possesses the function of inhibiting complement-mediated cell membrane damage by the present invention may be obtained by, for example, the following method.

In the screening for the gene coding for 1F5 antigen, human peripheral blood lymphocyte cDNA library, human T cell cDNA library, K562 cell cDNA library, human monocyte cDNA library, human placental cDNA library, etc. may be utilized, among which the placental cDNA library is particularly preferable. These libraries are purchased from Clonetech Inc. The cDNA library may also be prepared in a usual manner from any cell line expressing 1F5 antigen. In such case, MT-2 cDNA library and MOLT2 cDNA library are preferable.

*Escherichia coli* is infected with λ phage packaging such cDNA library, and cultured according to the method of Tomizawa et al. ("Experimental Techniques for Bacteriophages", Iwanami Shoten, Tokyo, pp. 99–174, 1970). The desired cDNA can be readily selected by screening resultant plaques the plaque hybridization technique ("Molecular Cloning", Cold Spring Harbor Laboratory, pp, 320–328, 1982) using as a probe an oligonucleotide having a base sequence deduced from the amino acid sequence of 1F5 antigen.

In the plaque hybridization, a partial cDNA fragment of the gene which encodes 1F5 antigen may be prepared by polymerase chain reaction (PCR) and used as the probe (Science, 239, 487–491, 1988). For example, PCR is carried out with +strand DNA primer$^{5'}$ CA A/G TG C/T TA C/T AA C/T TG C/T CC$^{3'}$ (17 nucleotides) corresponding to 27–32 of the amino acid sequence in FIG. 1 and −strand primer$^{5'}$ CA A/G TG C/T TC A/G AA C/T TTCCA$^{3'}$ (17 nucleotides) corresponding to 65–70 of the amino acid sequence in FIG. 1, to prepare as the probe at 131 bp-oligonucleotide fragment shown in FIG. 3 corresponding to 27–70 of the amino acid sequence in FIG. 1. A synthetic oligonucleotide may also be prepared according to the DNA base sequence estimated from the amino acid sequence of 1F5 antigen, and used as the probe.

Furthermore, the base sequence of the desired cDNA fragment may be determined by propagating the phage from a positive plaque on the above-mentioned screening as described by Tomizawa et al., by purifying DNA from the propagated phage according to the method of T. Maniatis et al. ("Molecular Cloning", Cold Spring Harbor Laboratory, 85, (1982)), then by cloning the DNA into a plasmid such as pUC18 or pUC19 after cleaving with a suitable restriction enzyme, e.g. Eco RI, and finally by subjecting it to the dideoxy method of Sanger et al. (Proc. Natl. Acad. Sci. USA, 74, 5463 (1977)).

An example of the cDNA fragment consists of a total of 387 base pairs (base sequence in FIG. 2), which code for the protein composed of 128 amino acids (the 25 amino acids at N-terminal serve as a signal peptide) containing the partial amino acid sequence (26–70) of 1F5 antigen shown in FIG. 1, and contains the entire length of the structure gene of 1F5 antigen.

The cDNA fragment obtained as described above may be inserted as it is or after modification of its 5'-terminal into a known vector by a conventional method at the downstream of a promoter. The expression vector with the inserted cDNA may be then introduced into known host cells such as E. coli, yeasts or animal cells by a conventional method.

The protein possessing the activity of inhibiting complement-mediated cell membrane damage may be expressed by the above cDNA in the host cells, isolated and purified there from by a conventional method.

The present invention will now be further illustrated by the following nonlimitative examples.

EXAMPLE 1

(1) Preparation of 1F5 antibody affinity Sepharose

CNBr-activated Sepharose 4B (Pharmacia) was soaked in 1 mM hydrochloric acid for 15–30 minutes. The resulting gel was washed repeatedly by aspiration on a glass filter with subsequent addition of 200 ml of 1 mM hydrochloric acid per g of dry gel.

The gel was then washed with coupling buffer (0.2M sodium hydrogencarbonate solution containing 0.5M sodium chloride, pH 8.5–8.7), 10 ml per g of dry gel. The washed gel was immediately transferred to a flask containing a 1F5 antibody solution in the coupling buffer to initiate a coupling reaction. The amount of 1F5 antibody in the reaction mixture was 5–10 mg per ml of swollen gel.

The coupling reaction was carried out overnight at 4° C. with constant and gentle stirring. After the reaction, the reaction mixture was transferred onto a glass funnel to recover unreacted antibody solution. The gel remaining on the funnel was then transferred to a flask containing 1M ethanolamine solution and allowed to stand for 16 hours at 4° C.

The resulting gel was transferred onto a glass funnel and aspirated. It was then washed by aspiration ten times with the coupling buffer, and subsequently ten times with 0.1M acetate buffer (pH 4.0) containing 0.5M sodium chloride. Finally, the gel was washed by aspiration three times using PBS to obtain 1F5 antibody affinity Sepharose.

(2) Preparation of human erythrocyte membrane (a) Washing of human erythrocytes

300–400 ml of human blood was centrifuged at 500×g for 15 minutes to separate red cells as a precipitate from a supernatant. To the precipitate, PBS containing 10 mM EDTA and 1 mM PMSF were added and centrifuged at 400–500×g for 15 minutes. The resulting precipitate was further washed with PBS containing 1 mM EDTA and 1 mM PMSF by centrifugation at 400–500×g for 15 minutes. The supernatant was removed to obtain a precipitate. Such washing processes were repeated till the supernatant became clear.

(b) Hemolysis of the erythrocytes and preparation of erythrocyte membrane

The washed erythrocytes obtained in (a) above were transferred to a flask containing 3–4 l of 10 mM Tris-HCl buffer (pH 7.5) containing 1 mM EDTA and 1 mM PMSF, hereinafter referred to as buffer A, and allowed to hemolyze with stirring overnight at 4° C.

The resulting mixture was centrifuged at 25,000×g for 30 minutes to collect an erythrocyte membrane fraction as a precipitate, which was resuspended in buffer A and centrifuged at 25,000×g for 30 minutes. This process was repeated until a faintly pink precipitate of red cell membrane was obtained.

(3) Solubilization of the erythrocyte membrane protein

The red cell membrane fraction obtained in (b) above was suspended in 500 ml of buffer A containing 1% n-octy-β-D-glucopyranoside (Sigma; NOG) and stirred overnight at 4° C.

The mixture was then centrifuged at 105,000×g for 30 minutes and the supernatant was collected. Solid ammonium sulfate was added gradually in limited quantities to this solution while stirring it at 4° C., to 30% ammonium sulfate saturation. After continued stirring at 4° C. for 2-3 hours, the solution was centrifuged at 10,000×g for 15 minutes. To the resulting supernatant, solid ammonium sulfate was added gradually in limited quantities to 60% saturation. This solution was stirred for 2-3 hours at 4° C., and centrifuged at 10,000×g for 15 minutes. The resultant precipitate was dissolved in a small volume of buffer a, and NOG was added to a final concentration of 0.1%. This solution was placed in a tube of dialysis membrane with an exclusion molecular weight of 3500 (Spectrum) and dialyzed overnight against buffer A containing 0.1% NOG and 0.15M sodium chloride.

(4) Affinity column chromatography

A column of the 1F5 antibody affinity Sepharose gel (bed volume, 5 ml) prepared as described in (1) above was equilibrated with buffer A containing 0.15M sodium chloride and 0.1% NOG. The solubilized membrane protein solution prepared in (c) above was adsorbed onto this column. The column was then washed by passing 1 l of buffer A containing 0.5M sodium chloride and 0.1% NOG through it. Subsequently, 100 ml of buffer A containing 0.15M sodium chloride and 0.1% CHAPS was made to flow through the column, followed by elution with 0.1M glycine-HCl buffer (pH 3.0) containing 0.1% CHAPS and 0.15M sodium chloride. The eluate was collected in 1-ml fractions and quickly neutralized by adding 1M glycine-NaOH buffer (pH 9.5). The eluate fractions were monitored for protein spectrophotometrically at $A_{280}$, and those positive for protein were pooled, concentrated by ultrafiltration (exclusion molecular weight; 10,000 or less), and dialyzed against PBS containing 0.1% CHAPS using the above dialysis membrane, to obtain 100-150 μg of the purified glycoprotein of the present invention.

(5) Properties of the glycoprotein of the present invention (a) Molecular weight: 20-25 Kd (12.5% SDS-PAGE under reductive or non-reductive condition)

Figure 4:
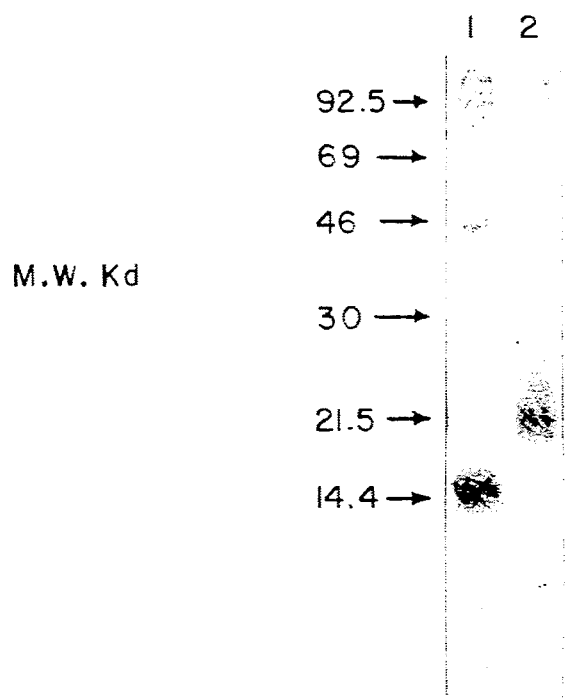
FIG. 4 is a photographic presentation of electrophoresis patterns (12.5% SDS-PAGE) of an endoglycosidase F-treated (1) and an untreated (2) samples of the glycoprotein provided by this invention.

(b) Its carbohydrate chain contains N-glycoside type carbohydrate chain:

Fifty μl of the glycoprotein (1 mg/ml) of the present invention was boiled with 50 μl of 2% SDS solution for 1 minute. To this solution, 1 unit of endoglycosidase F (Boehringer), 100 μl of 1M acetate buffer (pH 6.0), 100 μl of 0.25M EDTA (pH 7.5), 50 μl of 10% Triton X-100 (Sigma), 10 μl of 2-mercaptoethanol and 619 μl of distilled water were added, and stirred for 16 hours at 37° C. for reaction. Upon completion of the reaction, 200 μl of 50% trichloracetic acid solution was added and the mixture was allowed to stand in an ice bath for 10 minutes and centrifuged (10,000×g for 10 minutes). The resultant supernatant was discarded, and the precipitate was stirred with added 1 ml of cold acetone, then allowed to stand in an ice bath for 10 minutes and centrifuged (10,000×g for 10 minutes). The resulting supernatant was discarded. This process was repeated again, and the resulting precipitate was dissolved in a sample solution for SDS-PAGE. The resulting solution was boiled for 3 minutes and subjected to 12 5% SDS-PAGE A control was prepared in the same manner as described above except that endoglycosidase F was not contained in above reaction The result demonstrated on SDS-PAGE showed that the endoglycosidase F-treated sample had migrated as a band shifting by about 0.5 Kd to the lower-molecular weight side, compared with the control (FIG. 4).

It has thus indicated that the glycoprotein provided by the present invention contains N-glycoside type carbohydrate chain.

(c) It contains phosphatidylinositol:

MT2 cells, a human T cell leukemia virus-1 (HTLV-1) infected human T cell line, possessing the glycoprotein of this invention on their cell surface were used. MT2 cells were collected from an MT2 cell suspension in culture medium containing $1 \times 10^6$ cells by centrifugation (100-400×g for 5 minutes). The cells were resuspended in PBS, gently stirred and centrifuged as above, and the resulting supernatant was discarded. After repeating this process twice, the pellet consisting of $1 \times 10^6$ MT2 cells was resuspended in 150 μl of 10 mM Tris-HCl buffer (pH 7.5) containing 15 units of phosphatidylinositol-specific phospholipase C (PI-PLC; purified from *B. thrurinceinsis IAM* 12077 according to the method described in J. Biochem. 93, 1717 (1983)), 0.25 M sucrose; 10 mM EDTA and 0.1% bovine serum albumin, and allowed to stand for 90 minutes at 37° C. with a gentle stirring. Then, the reaction mixture was centrifuged with added 2 ml of PBS at 100 400×g for 10 minutes, and the resulting supernatant was discarded. This process was further repeated twice. Ten μl of sheep IgG (Cappel.) (10 mg/ml) was added to the cell pellet and stirred. The cell suspension was then allowed to stand for 10 minutes at room temperature, followed by three cycles of washing with PBS by centrifugation as described above. To the resulting precipitate, 20 μl of 1F5 antibody (concentration, $A_{280}$ 0.1) was added and stirred. This cell suspension was left for 20 minutes at room temperature, and washed three times with PBS. The cell pellet was stirred with added 20 μl of FITC-labeled anti-mouse IgG (Cappel.), then allowed to stand for 20 minutes at room temperature, and washed three times with PBS by centrifugation. The cell pellet was dispersed in 200 μl of Sheath solution (Fujisawa Pharmaceutical Co., Ltd.), and the resulting cell suspension was filtered through a nylon mesh filter. To the filtrate, 500 μl of Sheath solution was added and the mixture was subjected to flow cytometry using a FACS analyzer. A control was prepared with MT2 cells by the same treatment as described above but omitting the use of PI-PLC.

Figure 5:
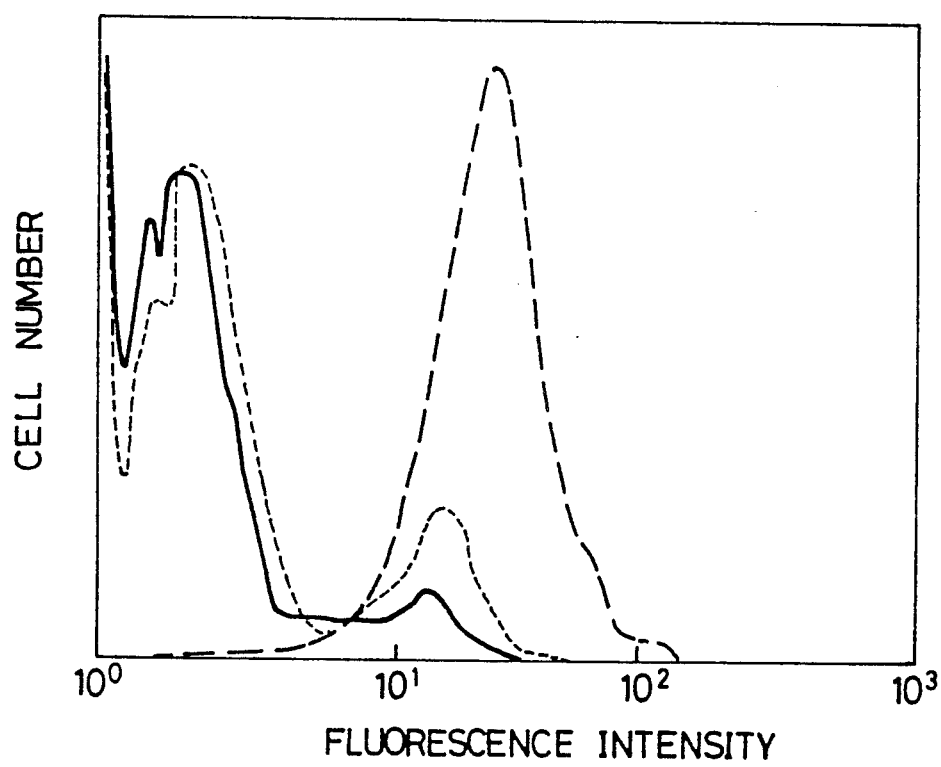
FIG. 5 illustrates liberations of the glycoprotein of the present invention from the cell surface of PI-PLC-treated cells ( . . . ) or untreated cells ( - - - ).

The PI-PLC-treated MT2 cells were shown to be negative for the glycoprotein of the present invention by 95% of the control cells (FIG. 5).

The above results have suggested that the glycoprotein of the present invention possesses phosphatidylinositol via which it is bound to the cell membrane.

(d) It has the activity of inhibiting human complement-mediated cell damage:

To 25 μl of a 2% guinea pig red cell suspension that had been thoroughly washed with PBS, for example, 12.5 μl of the glycoprotein of the present invention (at any given concentration of protein) and then 462.5 μl of PBS were added. The mixture was allowed to stand for 1 hour at 37° C. with a constant and gentle stirring. Following it, the mixture was centrifuged 100-400×g for 10 minutes with added 2 ml of Veronal buffer (Wako Pure Chemicals, Ltd.) containing 5 mM magnesium, 10 mM EGTA and 0.1% gelatin (Mg-EGTA-GVB), and the resulting supernatant was discarded. The precipitate was resuspended in 2 ml of Mg-EGTA-GVB and centrifuged as above. The supernatant was discarded, and the precipitate was again resuspended in added 100 μl of Mg-EGTA-GVB and 50 μl of normal human serum, and gently stirred for 60 minutes at 37° C. To this mixture, 1.0 ml of Veronal buffer containing 40 mM EDTA and 0.1% geletin was added and centrifuged at 100-400×g for 10 minutes. The resulting supernatant was spectrophotometrically analyzed at $A_{414}$, to determine the percent hemolysis of guinea pig erythrocytes by human complement. Bovine serum albumin at the same concentration was used for control in place of the glycoprotein of the present invention.

The guinea pig red cell hemolysis was inhibited by 90% in the presence of the glycoprotein of this invention added at a final concentration of 1 μg/ml. The results have indicated that the glycoprotein provided by the present invention is adsorbed onto the erythrocyte membrane and inhibits complement-mediated cell damage (FIG. 6).

(e) Isoelectric point: Analysis was carried out by isoelectric focusing with Ampholyne (Pharmacia) pI 3.5 to 10 in one dimension and by subsequent SDS-PAGE (12.5%) under non-reductive condition in the second dimension and demonstrated the formation of bands at pI values of about 5.0 (main band) and about 6.5.

(f) Its amino acid composition (using amino acid autoanalyzer):

---
Asp;20.2%, Thr;8.9%, Ser;3.1%,
Glu;10.6%, Gly;2.2%, Ala;6.2%,
Cys;0.6%, Val;4.5%, Ile;1.4%,
Leu;10.1%, Tyr;8.1%, Phe;6.4%,
Lys;9.1%, His;2.1%, Arg;3.0%,
Pro;3.5%
---

(g) Its partial amino acid sequence:

About 20 μg of the glycoprotein obtained in (d) above was subjected to a reverse phase high performance liquid-chromatography using a "Bakerbond Butyl" column (0.46×25 cm) (J. T. Baker) and eluted with a linear gradient of from 0% to 80% acetonitrile/isopropyl alcohol (3/7:v/v) mixture in 0.1% trifluoroacetic acid aqueous solution, over 40 minutes at a flow rate of 1 ml/min. Protein was detected spectrophotometrically at 215 nm. As seen in FIG. 7, approximately 13 protein fractions were obtained.

Of these protein fractions, the one eluted at about 36 minutes was dried in vacuo, then dissolved in 100 μl of Tris buffer (1M Tris-HCl buffer, pH 8.5, containing 5M guanidine hydrochloride), and reduced by the addition of 0.5 μl of 2-mercaptoethanol for 2 hours at 40° C. in nitrogen gas atmosphere. Subsequently, the resulting mixture was incubated with 1 mg of monoiodoacetic acid in nitrogen gas atmosphere at room temperature for 1 hour with protection from light, to obtain a reductive carboxymethylated protein.

The reductive carboxymethylated protein was subjected to reverse phase high performance liquid chromatography under the same conditions as above with a linear gradient elution of from 30% to 90% acetonitrile/isopropyl alcohol (3/7:v/v) mixture over 30 minutes. Detection made in the same manner as above disclosed approximately 3 protein fractions (FIG. 8).

Of the fractions thus obtained, the one eluted at about 21 minutes was dried in vacuo, and dissolved in 60 μl of 50% trifluoroacetic acid. The solution was transferred to a polyprene-coated glass filter and subjected to Edman degradation on an Applied Biosystems Model 470A sequencer.

PTH-amino acid was identified chromatographically on an "MCI gel ODS IHU" column (0.46×15 cm) (Mitsubishi Kasei Corporation) with single solvent elution of acetate buffer (10 mM acetate buffer, pH 4.7, containing 0.01% SDS and 38% acetonitrile) at a flow rate of 1.2 ml/min. at 43° C. Detection of PTH-amino acids was carried out by measurement of the absorbance at 269 nm.

Results of the analysis have showed the amino acid sequence at the amino-terminal of this protein is as follows:

---
Leu—Gln—Cys—Tyr—Asn—Cys—
Pro—Asn—Pro—Thr—Ala—Asp—
Cys—Lys—Thr—Ala—Val—X—X—
Ser—Ser—Asp—Phe—Asp—Ala—
X—Leu—X—Thr—Lys—Ala—Gly—
X—Gln—Val—Thr—Asn—Lys—X—
--- where X represents Cys or other amino acid residue.

EXAMPLE 2

(1) Preparation of polyclonal antibody to synthetic peptides (a) Preparation of antigen About 30 mg of keyhole limpet hemocyanin (KLH; Carbiochem) was dialysed against PBS at 4° C. overnight. The dialysate was diluted with 50 mM sodium borate-HCl buffer (pH 9.0) to a protein concentration of 30 mg/ml. Each of the below-described synthetic peptides (7.5 mg) was dissolved in 375 μl of 0.1M sodium phosphate buffer (pH 8.0), and 125 μl of the above-described KLH solution was added to each peptide solution.

(a) Leu-Gln-Cys-Tyr-Asn-Cys-Pro-Asn-Pro
(b) Thr-Ala-Asp-Cys-Lys-Thr-Ala-Val

To each of these mixtures, 5 μl of 25% glutaraldehyde (Sigma) solution was added and allowed to stand for 15 minutes at room temperature. Again, 5 μl of 25% glutaraldehyde solution was added to each mixture and allowed to stand for 15 minutes at room temperature.

Subsequently, 100 μl of 1M glycine-HCl buffer (pH 6.0) was added mixture and left for 10 minutes at room temperature. The mixtures were then dialyzed against PBS for 24 hours at 4° C., centrifuged at high speed, sterilized, dispensed in vials, and stored at 4° C.

(b) Preparation of antibody

Equal volumes of the two KLH-peptide conjugate preparations obtained above were combined and adjusted to a total protein concentration of about 2 mg/ml using PBS. A portion of this mixture was emulsified with an equal volume of Freund's complete adjuvant (Difco). Rabbits were immunized with the resulting emulsion by subcutaneous injections of 0.1-ml doses at four sites in the dorsal and into each footpad. The animals received additional immunizing doses subcutaneously at four sites in the dorsal 4 weeks afterwards. At 2 weeks after the second injections, 1 ml of the emulsified KLH-peptide conjugate (1 mg/ml) was injected subcutaneously at six sites in the dorsal for further immunization. The animals were totally bled 2-3 weeks after the last injections and their antisera were obtained. The antisera obtained were mixed with solid ammonium sulfate to 40% saturation while stirring, and the resultant mixture was further stirred for 2-3 hours at 4° C. The mixture was then centrifuged at 10,000×g for 15 minutes, and the resulting precipitate was dissolved in a small volume of PBS. This solution was applied to a Protein A Cellurofine (Seikagaku Kogyo) column equilibrated with PBS, washed with a sufficient amount of PBS, and eluted with 0.1M glycine-HCl buffer (pH 2.8). Eluted protein fractions were collected, immediately neutralized by the addition of 1M Tris solution, and concentrated by ultrafiltration (exclusion molecular weight: 30,000). The concentrated antibody solution was dialyzed against PBS at 4° C. overnight to obtain a purified polyclonal antibody.

(2) Purification of glycoprotein

An affinity Sepharose gel was prepared in the same manner and with the same reagents as in (2)-(d) of Example 1, except for using the polyclonal antibody obtained in (2) above in place of 1F5 antibody. The solubilized membrane protein solution obtained in (2) (a) to (c) of Example 1 was purified by affinity chromatography on a column of this polyclonal antibody Sepharose gel in the same manner as in Example 1. As a result, the glycoprotein of this invention having properties identical with those of the preparation in Example 1 was obtained.

EXAMPLE 3

Preparation of a partial cDNA fragment of 1F5 antigen by PCR method

The K562 cell cDNA which serves as a substrate may be prepared in an usual manner. That is, RNA possessing poly (A) was prepared from $1 \times 10^9$ K562 cells by the guanidine thiocyanate-cesium chloride method (DNA, 2, 329 (1983)) as follows. A starting material obtained from $1 \times 10^9$ K562 cells was solubilized in 40 ml of a solution consisting of 5M guanidine thiocyanate, 10 mM EDTA, 50 mM Tris-HCl (pH 7.0) and 8% (v/v) $\beta$-mercaptoethanol. 20 ml of the solubilized material was gently placed on 10 ml of 5.7M cesium chloride solution in a centrifuge tube, and centrifuged at 27,000 rpm for 20 hours in a Hitachi RPS28-2 Rotor, and the resulting precipitate of RNA was collected.

The RNA precipitate was dissolved in 10 ml of a solution consisting of 0.1% sodium laurylsulfate, 1 mM EDTA and 10 mM Tris-HCl (pH 7.5), then extracted with a phenol-chloroform mixture, and precipitated in ethanol. About 3.95 mg of the resulting RNA precipitate was dissolved in 1 ml of a solution consisting of 10 mM Tris-HCl (pH 8.0) and 1 mM EDTA, and incubated at 65° C. for 5 minutes, followed by addition of 0.1 ml of 5M sodium chloride. The resultant mixture was chromatographed on an Oligo[dt] Cellulose Column (P-L Biochemical) (column volume, 0.5 ml). The adsorbed mRNA possessing poly (A) was eluted with an eluant consisting of 10 mM Tris-HCl (pH 7.5) and 1 mM EDTA, and thereby approximately 100 μg of mRNA possessing poly (A) was obtained.

Ten μg of poly (A) mRNA was dissolved in 50 μl of RT buffer (20 mM Tris-HCl (pH 8.8), 0.1M potassium chloride, 12 mM magnesium chloride and 2 mM manganese chloride), and this solution was heated with added 8 μg of Oligo dT Primer-d (T) 12-18 (P-L Biochemical) at 95° C. for 3 minutes for denaturation. The resulting mixture was allowed to gradually cool to room temperature to permit annealing of Oligo dT primer. To this mixture, 10 μl of 10 mM 4NTP and 225 units of reverse transcriptase (Takara Shuzo Co., Ltd.) were added; and water was added to make up to a volume of 100 μl and incubated at 42° C. for 1 hour for reaction.

To 50 μl of the above reaction mixture, 2 μl of 10 mM NAD, 10 μl of 10 mM 4dNTP, 5 units of ribonuclease H, 1 unit of E. coli ligase, 6.3 units of E. coli DNA polymerase I and 10 μl of 10×conc. T4 DNA ligase buffer (0.1M Tris-HCl (pH 7.5), 0.1M DTT and 60 mM magnesium chloride) were added to make up to a total volume of 100 μl and incubated for 1 hour at 37° C. in order to synthesize a double strand DNA.

The double strand DNA obtained as above was extracted with an equal volume of water-saturated phenol. After removal of phenol from the aqueous layer with ether, it was precipitated in ethanol.

The precipitate obtained was dissolved in 50 μl of water, and 10 μl of 10×conc. T4 DNA polymerase buffer (0.33M Tris-acetic acid buffer (pH 7.9), 0.66M potassium acetate, 0.1M magnesium acetate and 5 mM DTT), 10 μl of 10 mM 4dNTP and 6 units of T4 DNA polymerase were added to this solution. The resulting mixture was made up to a volume of 100 μl, and incubated for 1 hour at 37° C. to obtain a double stranded DNA possessing blunt ends. This mixture was subjected to extraction with phenol as above, and after subsequent deproteinization, precipitated in ethanol to purity the DNA. The purified DNA was then allowed to dry in air.

Two μg of cDNA thus obtained was dissolved in 1 ml of H$_2$O to obtain a cDNA substrate. PCR was carried out with a Perkin Elmer Cetus DNA Thermal Cyster using Gene AMP ™ DNA Amplification Reagent Kit (Takara Shuzo) according to the directions provided by the manufacturer. That is, to 10 μl of the cDNA substrate (equivalent to 20 ng of the cDNA), 10 μl of 10×conc. reaction buffer (500 mM potassium chloride, 100 mM Tris-HCl (pH 8.3), 15 mM magnesium chloride and 0.1% (w/v) gelatin), 16 μl of 1.25 mM 4d NTP, 5 μl of +strand DNA primer 5' CA A/G TC C/T TA C/T AA C/T TG C/T CC 3' (17 nucleotide) corresponding to the amino acid sequence 27-32 in FIG. 1 as 20 μM primer #1, 5 μl of 20 μM −strand DNA primer 5' CA A/G TG C/T TC A/G AA C/T TTCCA 3' (17 nucleotide) corresponding to the amino acid sequence 65-70 in FIG. 1 as (20 μM) primer #2 and 0.5 μl of Taq DNA polymerase were added. This mixture was made up to a volume of 100 μl, pretreated for 10 minutes at 94° C., and subjected to reaction by 35 cycles of successive incubation for 1 minute at 94° C. (denaturation step), for 2 minutes at 42° C. (annealing step) and for 1.5 minutes at 72° C. (Elongation step). The reaction mixture was further incubated for 7 minutes at 72° C., and then precipitated in ethanol. This precipitate was dissolved in 50 μl of water. To this solution, 10 μl of T4 DNA polymerase buffer (0.33M Tris-acetic acid (pH 7.9), 0.66M potassium acetate, 0.1M magnesium acetate and 5 mM DTT), 10 μl of 10 mM 4d NTP and 6 units of T4 DNA polymerase were added. The resultant mixture was made up to a volume of 100 μl, and incubated for 1 hour at 37° C. to obtain double stranded blunt ends. Analysis of the reaction mixture by 5% polyacrylamide gel electrophoresis revealed a band of about 150 bp. The band of about 150 bp was cut out of the polyacrylamide gel strip and cDNA contained therein was inserted into Sma I site of cloning vector pUC12 by the dideoxy method, and its base sequence was determined using commercially available primers 5'CAGGAAACAGCATGAC3' and 5'AGTCACGACGTTGTA3'. As a result, the base sequence of the said PCR fragment was found to be as shown in FIG. 3, and the amino acid sequence estimated by the 131-bp fragment corresponded to the sequence 27-70 in FIG. 1 and entirely coincided with the amino acid sequence determined from the purified 1F5 antigen protein. The inserted fragment was cleaved at Kpn I and BAMH I out of this recombinant plasmid purified and cut out of the acrylamide gel, and radiolabeled by the multiprimer DNA labeling technique (Anal. Biochem, 132, 6 (1983)) to obtain a probe for cDNA library screening. That is, 100 ng of this DNA fragment was dissolved in water sufficient to make 32 μl, denatured by heating for 2 minutes at 95° C., and immediately cooled on an ice bath. To this solution, 1 μl of OLB buffer [0.25M Tris-HCl (pH 8.0), 0.025M magnesium chloride, 0.4% β-mercaptoethanol, 0.1 mM dATP, 0.1 mM dTTP, 0.1 mM dGTP, 1M HEPES (pH 6.6), 10 μl of oligo primer p dN$_6$ (P-L Biochemical, 15 units )] 2 μl of 10 mg/ml bovine serum albumin, 5 μl of α-$^{32}$Pd CTP (3000 ci/mmol) and 2 units of DNA polymerase large (Klenow) fragment was added and the mixture was incubated for 30 minutes at 37°. This reaction mixture was used as a probe.

EXAMPLE 4

Screening of cDNA for 1F5 antigen

Thirty-four-week-old human placenta cDNA-λ gt11 library (Clonetech Inc.) was used as a λ phage cDNA library for screening. E. coli strain Y1090 was infected with the cDNA library for plaque formation according to the directions provided by the manufacturer. Using the probe prepared in Example 3 above, the below-described seven positive plaques were obtained ultimately out of approximately 1,500,000 plaques by plaque hybridization technique.

E. coli strain Y1090 infected with 80 gt11 (Proc. Natl. Acad, Sci. USA, 80, 1194, (1983)) was inoculated together with a soft agar overlay maintained at 42° C. in Petri dishes, and incubated at 42° C. for 8 hours. The dishes were than cooled for 30 minutes at 4° C., and a nitrocellulose filter (S&S Inc.; BA-83; pore size, 0.2 μm) was placed on each dish and allowed to stand for 2 minutes. Subsequently, another filter was placed on that filter and allowed to stand for 5 minutes. Both nitrocellulose filters were immersed twice for 20 seconds each in a solution of 0.1N sodium hydroxide and 1.5M sodium chloride. The filters were then neutralized by being immersed twice for 20 seconds each in a solution of 2×SSCP (30 mM sodium citrate, 240 mM sodium chloride, 26 mM monopotassium phosphate and 2 mM EDTA, pH 7.2) and 0.2M Tris-HCl (pH 7.4), and then dried in air for 2 hours at 80° C. Subsequently, they were soaked in 2×SSC (450 mM sodium chloride and 45 mM sodium citrate) for 30 minutes at 65° C. From the filters sufficiently moistened, the bacterial cells were evenly removed with a sponge and the resulting filters were immersed in a solution consisting of 3×SSC and 10×Denhardt's mixture (0.2% Ficoll, 0.2% polyvinylpyrrolidone and 0.2% BSA) for 1 hour at 65° C. They were then immersed in a hybridization solution [133 Solution A (50 mM Tris-HCl (pH 7.8), 10 mM EDTA, 1M sodium chloride and 10×Denhardt's mixture), 0.1% SDS and herring testis DNA at 250 μg/ml] for 30 minutes at 65° C. The filters thus treated were placed in a polyvinyl bag with the hybridization solution containing the PCR probe at 0.1 ng/ml was added, and the bag was sealed. The filters in the bag were subjected to hybridization by incubation for 15 hours at 50° C. They were then washed twice with 2×SSC-0.1% SDS mixture for 5 minutes each at room temperature, followed by washing for 15 minutes at 60° C., and they were subsequently washed twice with 0.1×SSC-0.1% SDS mixture for 15 minutes each at 60° C. The filters were wrapped up in polyvinylidene chloride film (Saran Wrap ®; Asahi Chemical Co., Ltd.) and subjected to autoradiography.

By this primary screening, 33 phages showing a positive signal were isolated. These positive plaques were subjected to three cycles of single plaque isolation by the same plaque hybridization procedure. Seven positive plaques were finally obtained.

These phages were cultured in large quantities, from which DNA was purified E. coli strain Y1090 was grown overnight in 10 ml of NZ medium prepared by dissolving 10 g of NZ amine, 5 g of sodium chloride and 5 mM of magnesium chloride in 1000 ml of water and by adjusting the solution to pH 7.2. One ml of the overnight culture was infected with the phage at a multiplicity of infection (m.o.i.) of 0.1 and incubated for 10 minutes at 37° C., then transferred to a flask containing 1 liter of NZ medium, and incubated for 7-8 hours at 37° C. with a constant shaking until the bacteria became lyzed. Five ml of chloroform was then added to the culture, which was further incubated with shaking for 30 minutes. The bacterial cell debris was removed from the culture by centrifugation at 650 r.p.m. for 10 minutes. In to the resulting supernatant, 29 g of sodium chloride and 70 g of polyethyleneglycol were dissolved thoroughly, and the mixture was allowed to stand overnight at 4° C. It was then centrifuged at 6,500 r.p.m. for 20 minutes. The resulting precipitate was collected, well drained and dissolved in 20 ml of TM buffer consisting of 10 mM Tris-HCl (pH 7.5) and 5 mM magnesium chloride. The mixture was incubated for 1 hour at 37° C. with added DNase I and RNase A both at 10 μg/ml.

The reaction mixture was stirred with added 20 ml of chloroform, followed by removal of the chloroform from an aqueous layer by dissolving polyethyleneglycol therein. The aqueous layer remained was ultracentrifuged at 28,000 r.p.m. for 60 minutes to collect the pellet of phage particles. The pellet was dissolved in 1 ml of TM buffer and subjected to cesium chloride density gradient centrifugation at 33,000 r.p.m. for 20 hours, to obtain a fraction containing phage particles of p=1.45 to 1.50. The fraction was dialyzed against TM buffer overnight, followed by incubation for 1 hour at 37° C. with added proteinase K at 100 μg/ml. Subsequently, the mixture was subjected to a gentle phenol extraction by adding an equal volume of water-saturated phenol. It was then centrifuged at 6,500 r.p.m. for 10 minutes, and the aqueous layer was transferred to a dialysis tube and dialyzed against water at 4° C. overnight. Approximately 5 mg of DNA was thus obtained.

These phage DNAs, when digested with Eco RI, all proved to possess the inserted fragment of 1.2-1.8 Kb. Digestion patterns of these preparations with various restriction enzymes showed that all these preparations had a common Eco RI-Bam HI fragment of about 500 bp. Of these phage DNA preparations, four DNA preparations were selected and their Eco RI and Eco RI.-BAM HI fragments were recloned into the Eco RI site and Eco RI-Bam HI site of the cloning vector pUC119, respectively. Their base sequences were determined by the dideoxy method using commercially available primers 5'CAGGAAACAGCTATGAC3' and 5'AGTCACGACGACGTTGTA3', and products synthesized +strand DNA primer 5'CAGTGCTACAA C/T TG C/T CC3' corresponding to the amino acid sequence 27-32, −strand DNA primer 5'GTCAGCAGTTGGGTTAGG3', corresponding to the amino acid 42-47, +strand DNA primer 5'GTGTATAACAAGTGTTGG3' corresponding to the amino acid sequence 60-65 and −strand DNA primer 5'CAGTGCTCGAACTTCCA3' corresponding to the amino acid sequence 65-70 in FIG. 1. All the four cDNA preparations tested exhibited the base sequence in FIG. 2, that is, a complete full-length cDNA of the gene of 1F5 antigen protein consisting of total lengths of 387 base pairs which code the protein consisting of 128 amino acids containing a signal peptide of its N-terminal 25 amino acids. Meanwhile, the fact that the primer base sequence of the DNA fragment obtained by the PCR method differed from that of the resultant cDNA may be explained by that the primer distinct in base sequence from the cDNA was selected and amplified due to the use of the primer mixture in PCR.

What is claimed is:

1. A substantially pure glycoprotein free of human cell membranes, derived from human cell membranes, which has a molecular weight of 20 to 25 Kd as estimated by SDS polyacrylamide gel electrophoresis under either non-reducing or reducing conditions, and contains carbohydrate chains with at least one N-glycoside and phosphatidylinositol, and which inhibits complement-mediated cell membrane damage, and wherein said glycoprotein has the following amino acid sequence:

| Met | Gly | Ile | Gln | Gly | Gly |
|-----|-----|-----|-----|-----|-----|
| Ser | Val | Leu | Phe | Gly | Leu |
| Leu | Leu | Val | Leu | Ala | Val |
| Phe | Cys | His | Ser | Gly | His |
| Ser | Leu | Gln | Cys | Tyr | Asn |
| Cys | Pro | Asn | Pro | Thr | Ala |
| Asp | Cys | Lys | Thr | Ala | Val |
| Asn | Cys | Ser | Ser | Asp | Phe |
| Asp | Ala | Cys | Leu | Ile | Thr |
| Lys | Ala | Gly | Leu | Gln | Val |
| Tyr | Asn | Lys | Cys | Trp | Lys |
| Phe | Glu | His | Cys | Asn | Phe |
| Asn | Asp | Val | Thr | Thr | Arg |
| Leu | Arg | Glu | Asn | Glu | Leu |
| Thr | Tyr | Tyr | Cys | Cys | Lys |
| Lys | Asp | Leu | Cys | Asn | Phe |
| Asn | Glu | Gln | Leu | Glu | Asn |
| Gly | Gly | Thr | Ser | Leu | Ser |
| Glu | Lys | Thr | Val | Leu | Leu |
| Leu | Val | Thr | Pro | Phe | Leu |
| Ala | Ala | Ala | Trp | Ser | Leu |
| His | Pro. | | | | |

* * * * *